(12) United States Patent
Elmann et al.

(10) Patent No.: US 11,793,767 B2
(45) Date of Patent: Oct. 24, 2023

(54) GERANIUM OIL AND CONSTITUENTS THEREOF FOR TREATMENT OF NEURODEGENERATIVE DISEASES

(71) Applicant: The State of Israel, Ministry of Agriculture & Rural Development, Agricultural Research Organization, Rishon Lezion (IL)

(72) Inventors: Anat Elmann, Rehovot (IL); Uzi Ravid, Haifa (IL)

(73) Assignee: THE STATE OF ISRAEL, MINISTRY OF AGRICULTURE & RURAL DEVELOPMENT AGRICULTURE RESEARCH ORGANIZATION, Rishon Lezion (IL)

( * ) Notice: Subject to any disclaimer, the term of this patent is extended or adjusted under 35 U.S.C. 154(b) by 302 days.

(21) Appl. No.: 16/795,709

(22) Filed: Feb. 20, 2020

(65) Prior Publication Data
US 2020/0188320 A1    Jun. 18, 2020

Related U.S. Application Data

(63) Continuation of application No. 14/399,178, filed as application No. PCT/IB2013/053657 on May 7, 2013, now abandoned.

(60) Provisional application No. 61/688,050, filed on May 7, 2012.

(51) Int. Cl.
| | |
|---|---|
| A61K 36/185 | (2006.01) |
| A23L 27/12 | (2016.01) |
| A23L 33/105 | (2016.01) |
| A61K 31/045 | (2006.01) |
| A61K 31/122 | (2006.01) |
| A23L 33/115 | (2016.01) |

(52) U.S. Cl.
CPC ............ *A61K 31/045* (2013.01); *A23L 27/12* (2016.08); *A23L 33/105* (2016.08); *A23L 33/115* (2016.08); *A61K 31/122* (2013.01); *A61K 36/185* (2013.01); *A23V 2002/00* (2013.01)

(58) Field of Classification Search
CPC .... A61K 36/18; A61K 31/045; A61K 31/122; A61K 36/185; A23L 27/12; A23L 33/105; A23L 33/115; A23V 2002/00; A61P 25/16; A61P 25/28
See application file for complete search history.

(56) References Cited

U.S. PATENT DOCUMENTS

| | | | |
|---|---|---|---|
| 6,177,472 B1 | 1/2001 | Wilson | |
| 2007/0166404 A1 | 7/2007 | Chang et al. | |
| 2007/0219131 A1 | 9/2007 | Ben-Sasson | |
| 2008/0268078 A1 | 10/2008 | Su | |
| 2009/0012162 A1 | 1/2009 | D'Alessio | |
| 2014/0045858 A1 | 2/2014 | Wang | |

FOREIGN PATENT DOCUMENTS

| | | | | |
|---|---|---|---|---|
| CN | 101677973 A | | 3/2010 | |
| CN | 102151268 A | * | 8/2011 | ........... A61K 31/473 |
| JP | S60190737 A | | 9/1985 | |
| JP | 2006241044 A | * | 9/2006 | |
| JP | 2007302572 A | | 11/2007 | |
| JP | 2009114090 A | | 5/2009 | |
| KR | 20110134961 A | | 12/2011 | |
| WO | 2005063213 A1 | | 7/2005 | |

OTHER PUBLICATIONS

Elmann A, et al, "Anti-neuroinflammatory effects of geranium oil in microglial cells" J. Funct. Foods, Jan. 7, 2010, 2(1), pp. 17-22; doi: 10.1016/j.jff.2009.12.001. (Year: 2010).*
Ravid et al. Flavour and Fragrance Journal, vol. 7. p. 235-238 (Year: 1992).
Rydzewski, R.M. "1.4.8 Chiral Switching" in Real World Drug Discovery, pp. 42-43 (Year: 2008).
Nguyen et al. Int J Biomed Sci. Jun. 2006; 2(2): 85-100. (Year: 2006).
Debboun et al. Insect Repellents: Principles, Methods, and Uses. (2007) pp. 282 (Year: 2007).
Kirk-Othmer. Kirk-Othmer Chemical Technology of Cosmetics. (2013) 1 page. (Year: 2013).
Perry et al. "In-vitro Inhibition of Human Erythrocyte Acetylcholinesterase by Salvia lavandulaefolia Essential Oil and Constituent Terpenes". Journal of Pharmacy and Pharmacology, Jul. 2000, vol. 52, No. 7, pp. 895-902.
Elman et al. "Anti-neuroinflammatory effects of geranium oil in microglial cells". Journal of 6, 16-21 Functional Foods, Jan. 7, 2010, vol. 2, No. 1, pp. 17-22. Jan. 7, 2010 (Jan. 7, 2010).
Lee et al. Fumigant toxicity of volatile natural products from Korean spices and medicinal 1,4,11 plants towards the rice weevil, (L). Crop protection, May 1, 2001, vol. 20, No. 4, pp. 317-320. May 1, 2001 (May 1, 2001).
Jukic Mila et al, "In vitro acetylcholinesterase inhibitory properties of thymol, carvacrol and their derivatives hymoquinone and thymohydroquinone", Phytotherapy Research, (200703), vol. 21, No. 3, doi:10.1002/PTR.2063, ISSN 0951-418X, pp. 259-261, XP002752072 *the whole document.

* cited by examiner

*Primary Examiner* — Aaron J Kosar
(74) *Attorney, Agent, or Firm* — BROWDY AND NEIMARK, PLLC

(57) ABSTRACT

The invention relates to the use of effective amount of *Pelargonium graveolens* essential oil or extract or constituents thereof selected from a group consisting of: (S)(−) citronellol, linalool, menthone and isomenthone or any combination thereof, in the preparation of a medicament for treating a mammal suffering from or susceptible to a neurodegenerative condition which can be improved or prevented by inhibition of acetylcholinesterase (ACliE).

5 Claims, 6 Drawing Sheets

GERANIUM OIL AND CONSTITUENTS THEREOF FOR TREATMENT OF NEURODEGENERATIVE DISEASES

FIELD OF THE INVENTION

The invention relates to geranium oil formulations for treating neurodegenerative diseases, particularly to neurodegenerative diseases which can be improved or prevented by inhibition of acetylcholinesterase (AChE).

DESCRIPTION OF THE STATE OF THE ART

Essential oils are a folk medicine and recently their use has expanded worldwide to include therapy against various kinds of inflammatory diseases, such as allergy, rheumatism, arthritis and bronchitis. These activities have mainly been recognized through clinical experience, but have been little elucidated experimentally.

Geranium oil is one of the most important natural raw materials in the fragrance industry. It is used for creating rosy notes, especially in soap. The main cultivation areas are Reunion and Madagascar (Bourbon type), Morocco and Egypt (North African type), and China.

Geranium oil is obtained by steam distillation of the flowering herb *Pelargonium graveolens* l'Heritier ex Aiton, *P. roseum* Wilidenow, and other non-defined hybrids that have developed into different ecotypes in different geographical regions. The oil is amber to greenish-yellow liquid with the characteristic roselike odor of the plant.

Maruyama et al., *Mediators Inflamm.* 2006; 2006(3): 62537 teach that injection of geranium oil suppressed the carrageenan-induced footpaw edema and increase in tissue myeloperoxidase activity, and repeated administration of the oil suppressed collagen-induced arthritis.

According to Abe et al, *Mediators of Inflammation*, 13(1), 21-24 (February 2004), leukocyte recruitment into the peritoneal cavity in mice was suppressed by intraperitoneal injections of *Pelargonium asperum*.

US Publication 20080268078 reports the inhibition and/or reduction of nitric oxide (NO) and/or prostaglandin $E_2$ synthesis, by administering a geranium plant extract comprises butylidene, phthalide, citronellol and geraniol.

According to Elmann et al, *Journal of Functional Foods* 2 (2010) 17-22, the essential oil of geranium was tested for its anti-neuroinflammatory effects using primary cultures of microglial cells. Geranium oil inhibited NO production, as well as the expression of the proinflammatory enzymes cyclooxygenase-2 (COX-2) and induced nitric oxide synthase (iNOS) in primary cultures of activated microglial cells.

Parkinson's disease (PD) is the second most frequent degenerative disorder after Alzheimer's disease. Clinically, its cardinal features include tremor, muscle rigidity, slowness of voluntary movement and postural instability. Although PD neuropathology encompasses a number of different neurotransmitter pathways the disabling manifestations cited above are attributed primarily to a deficit in brain dopamine (*Nat Protoc.* 2007; 2(1):141-51). Among the different dopaminergic systems of the brain, the ascending nigrostriatal pathway has been consistently identified as the most severely damaged in PD, underlined by the death of the nigrostriatal dopaminergic neurons.

Alzheimer's disease is associated with a selective loss of cholinergic neurons in the brain (Davies and Maioney, *Lancet.* 1976 Dec. 25; 2(8000):1403; Whitehouse et al., *Ann Neurol.* 1981 August; 10(2): 122-6). The losses are accompanied by decreases in the neurotransmitter acetylcholine as well as in the respective enzymes that synthesize and degrade acetylcholine, choline acetyltransferase and acetylcholinesterase (AChE) (Perry et al, *Lancet.* 1977 Jan. 2¾1 (8004): 189; Bowen et al., *J Neurol Set* 1982 December; 57(2-3):191-202). These observations stimulated a cholinergic hypothesis of Alzheimer's disease (Bartus et al., *Science.* 1982 Jul. 30; 217(4558):408-14), which postulates that at least some of the cognitive decline experienced by patients with the disease results from a deficiency in acetylcholine and thus in cholinergic neurotransmission. This hypothesis suggested that inhibitors of AChE might elevate levels of acetylcholine in the brains of these patients and reverse the cognitive decline (Muramoto et al., *Arch Neurol.* 1979 August; 36(8):501-3), and experimental evidence has supported this suggestion (Camps et al, *Mol Pharmacol.* 2000 February; 57(2):409-17).

Cholinesterase inhibitors, such as Donepezil®, Rivastigmine® and Galantamine®, are used as standard therapy for mild to moderate Alzheimer's disease and show therapeutic effect of this class of medications on the symptoms of Alzheimer's disease.

Umezu T, *Phytother. Res.* 26: 884-891 (2012) teaches that *Pelargonium graveolens* oil did not produce any effect on discrete shuttle-type conditioned avoidance response in mice (abstract). The discrete shuttle-type conditioned avoidance response is useful for distinguishing CNS stimulants and CNS depressants.

It has now surprisingly been found that *Pelargonium graveolens* oil and constituents thereof have good effect in preventing and improving neurodegenerative symptoms.

SUMMARY OF THE INVENTION

The present invention relates to the use of *P. graveolens* essential oils or extracts for the treatment of neurodegenerative diseases.

It has been found that essential oils of *P. graveolens* serve as AChE inhibitor. It has also been found that constituents of *P. graveolens* selected from the group consisting of (S)(-)-citronellol, linalool, menthone and isomenthone serve as AChE inhibitors.

The inventors have found that only the enantiomer (S)(-) citronellol but not (R)(+)citronellol could inhibit the enzymatic activity of acetyl cholinesterase. These results are quite unexpected when comparing them to the effect of the same enantiomers on Reactive Oxygen Species (ROS) in microglial cells. While both enantiomers show significant reduction on ROS production (FIG. 1), only the enantiomer (S)(-)citronellol shows inhibition of enzymatic activity of acetyl cholinesterase (FIGS. 2 and 3).

The present invention relates to the use of effective amount of any one of the *Pelargonium graveolens* constituents selected from a group consisting of: (S)(-)citronellol, linalool, menthone and isomenthone or any combination thereof, in the preparation of a medicament for treating a mammal suffering from or susceptible to a neurodegenerative condition which can be improved or prevented by inhibition of acetylcholinesterase (AChE).

The present invention further relates to the use of effective amount of any one of the above *Pelargonium graveolens* constituents wherein said neurodegenerative condition is Alzheimer's disease, Parkinson's disease, parkinsonian dementia (PDem), Parkinson's disease dementia (PDD), dementia with Lewy bodies (DLB), anorexia nervosa, traumatic brain injury (TBI), and Parkinson's disease falling short of dementia (CIND-PD).

The present invention further relates to *Pelargonium graveolens* essential oil for use in treating Parkinson's disease, parkinsonian dementia (PDem), Parkinson's disease dementia (PDD), dementia with Lewy bodies (DLB), anorexia nervosa, traumatic brain injury (TBI), and Parkinson's disease falling short of dementia (CIND-PD).

DETAILED DESCRIPTION OF THE INVENTION

Figure 1:
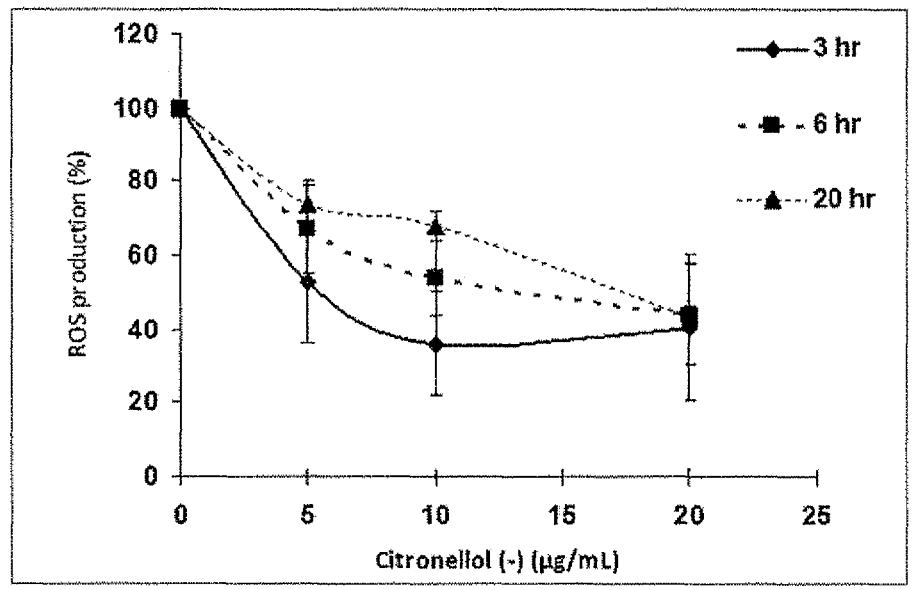
FIG. 1 shows the effect of enantiomers (S)(−)citronellol (FIG. 1A) and (R)(+)citronellol (FIG. 1B) of Geranium oil on the peroxyl radical-induced oxidation of DCFH in primary microglial cells.
Figure 1:
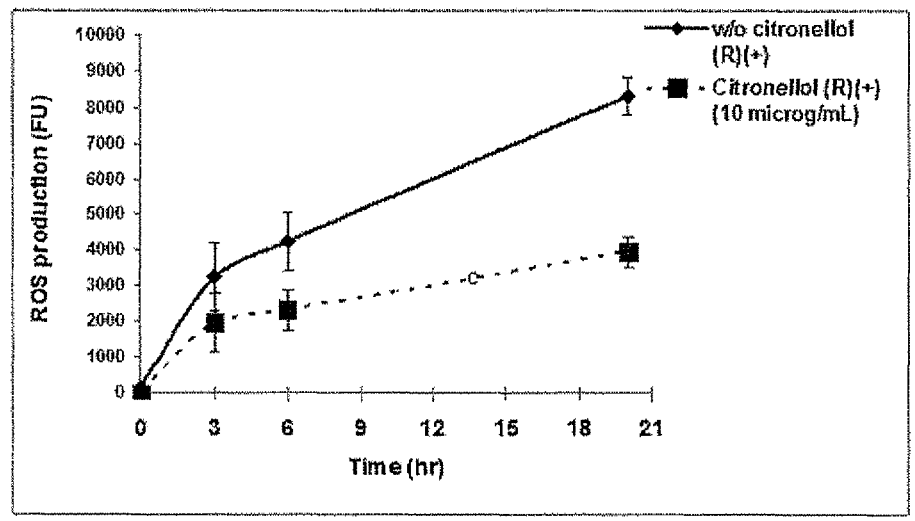

Essential oil or extract of *P. graveolens* or constituents thereof selected from the group consisting of (S)(−)-citronellol, linalool, menthone and isomenthone is expected to cause a significant increase in concentrations of acetylcholine in the cerebral cortex and/or hippocampus and/or striatum and/or whole brain of a patient. Accordingly, therapeutic effect of various diseases associated with AChE inhibition and with an increase in concentrations of acetylcholine, may be achieved by pharmaceutical compositions of the present invention.

Extracts of *P. graveolens* may be prepared using conventional methods. One exemplary extraction method is summarized below. In summary form, the method includes: (1) drying the selected plant parts and milling the dried plant parts to a fine powder; (2) mixing the plant powder to an extraction solvent; (3) removing the plant remnants by centrifugation and collecting the solvent supernatant; (4) removing the remaining solvent and water in the supernatant by rotary evaporation and drying. One of ordinary skill in the art would realize that the method may be modified appropriately, e.g., for the transition from a small-, or laboratory-, scale to a commercial-scale method. The drying process may not be needed for extraction purposes. Fresh plant material may be directly subjected to solvent extraction without the drying step. Dried plant parts do offer an advantage in terms of transport and storage of the crop; however, the activity of the extract from air-dried plants may be lower than the activity of freeze-dried extracts due to possible increase in breakdown of components in the air-dried counterparts.

The extraction solvent may be a mildly polar fluid. The "mildly polar" fluid means a fluid that is slightly to moderately polar, as would be understood in the art. Mildly polar as used herein means moderately irregular distribution of electrons that is characterized by a weak to average degree of hydrophilicity. A mildly polar fluid includes all straight chain and branched primary alcohols and chemical derivatives thereof, provided that the additional chemical groups do not destroy the polarity of the fluid or increase the polarity of the fluid to the level of water, which is expressly excluded from the definition of a mildly polar fluid. Preferred mildly polar fluids are liquids, such as the lower molecular weight, straight chain, primary alcohols (e.g., ethanol). Water is not a mildly polar fluid, but is a highly polar aqueous fluid. However, a mixture of water and a mildly polar fluid (e.g., ethanol) is itself a mildly polar fluid. An example of the latter fluid is 60% ethanol. A variety of mildly polar fluids, such as alcohols, may be used to extract efficacious materials from the selected plant parts, including methanol, ethanol, and isopropanol. When alcohol is used, the resulting product is an ethanolic extract.

In a preferred embodiment, *P. graveolens* will be in the form of essential oil. The essential oil may be either steam-distilled or hydro-distilled from the fresh herb foliage for one hour in a 130 L direct steam pilot plant apparatus or in a modified clevenger apparatus respectively.

As already outlined, inhibitors of AChE might elevate levels of acetylcholine in the brains of these patients and reverse their behavioral decline.

In a preferred embodiment, the plant essential oil or extract of *P. graveolens* is the sole active ingredient in a composition for treating neurodegenerative disease. In another preferred embodiment, the plant essential oil or extract of *P. graveolens* is the sole active ingredient for treating neurodegenerative disease.

In another embodiment, any combination of the active constituents that is, only part of the active constituents (S)(−)citronellol, linalool, menthone and isomenthone are used for treating neurodegenerative disease.

Choline-esterase inhibitors (such as donepezil, tacrine, rivastigmin and galantamine) are widely used for improving cognition in Alzheimer's disease and show promising clinical result in Dementia with Lewy Bodies.

Pathology reports have shown that cholinergic forebrain neuronal losses in parkinsonian dementia (PDem) are equal to or greater than that in Alzheimer disease (AD). Bohnen et at, *Arch Neurol.* 2003; 60(12): 1745-1748 shows that compared with controls, mean cortical AChE activity was lowest in patients with PDem (−20.0%), followed by patients with Parkinson disease without dementia (−12.9%; $P<0.001$). In vivo cortical acetylcholinesterase (AChE) activity in healthy control subjects and in patients with mild AD, PDem, and Parkinson disease without dementia using AChE positron emission tomography has been determined. Therefore, an embodiment of the invention is the use of *P. graveolens* essential oil or extract, (S)(−)-citronellol, linalool, menthone and isomenthone in the preparation of a medicament in the treatment of parkinsonian dementia (PDem) and Parkinson disease without dementia.

Bohnen et at, *J Neurol Neurosurg Psychiatry* 2007; 78:641-643 investigated the relationship between ratings of depressive symptoms and in vivo cortical acetylcholinesterase (AChE) activity in subjects with Parkinson's disease (PD) and parkinsonian dementia (PDem). Subjects with PD and with PDem, underwent [$^{11}$C]methyl-4-piperidinyl propionate AChE positron emission tomography imaging and clinical assessment including the Cornell Scale for Depression in Dementia (CSDD). Bohnen et al. concludes that depressive symptomotology is associated with cortical cholinergic denervation in PD.

According to Ballard et at, *Drugs Aging.* 2011 Oct. 1; 28(10):769-77, randomized controlled trials (RCTs) of the cholinesterase inhibitor rivastigmine have indicated modest but significant benefits in cognition, function, global outcome and neuropsychiatric symptoms in both Parkinson's disease dementia (PDD) and dementia with Lewy bodies (DLB). Therefore, another embodiment is the use of *P. graveolens* essential oil or extract, (S)(−)-citronellol, linalool, menthone and isomenthone in the preparation of a medicament in the treatment of Parkinson's disease dementia (PDD) and dementia with Lewy bodies (DLB).

Patients with anorexia nervosa present compromised affectivity, characterized by hypomanic, manic and depressive symptoms, and their cholinergic system is altered with a decrease in the release of acetylcholine (Expert Opin. Investig. Drugs (2009) 18(5):569-571). Therefore, another embodiment of the invention is the use of *P. graveolens* essential oil or extract, (S)(−)-citronellol, linalool, menthone and isomenthone in the preparation of a medicament in the treatment of anorexia nervosa.

Memory impairments following traumatic brain injury (TBI) are well recognized and can be difficult to treat, particularly for those TBI survivors who experience persistent amnesia. Morey et al., *Brain Injury*, VOL. 17, NO. 9. September 2003, 809-815 reports that the acetylcholinesterase inhibitor, Aricept® (donepezil hydrochloride), may potentially be useful in treating such memory problems. According to Morey et al., Aricept®, which increases the availability of acetylcholine at the post-synaptic receptors by inhibiting acetylcholinesterase (AChE) function in the central nervous system has been shown to be effective in treating symptoms of memory loss in patients with AD and, more recently, with TBI. Therefore, another embodiment of the invention is the use of *P. graveolens* essential oil or extract, (S)(−)-citronellol, linalool, menthone and isomenthone in the preparation of a medicament in the treatment of memory loss in patients with AD and in the treatment of TBI.

According to Rolinski M et al. *Cochrane Database Syst Rev.* (2012), currently available evidence supports the use of cholinesterase inhibitors in patient with Parkinson's disease dementia PDD and cognitive impairment in Parkinson's disease falling short of dementia (CIND-PD), with a positive impact on global assessment, cognitive function, behavioural disturbance and activities of daily living rating scales. Therefore, another embodiment of the invention is the use of *P. graveolens* essential oil or extract, (S)(~)-citronellol, linalool, menthone and isomenthone in the preparation of a medicament in the treatment of Parkinson's disease dementia (PDD) and CIND-PD.

Thus, according to the present invention, any neurodegenerative condition susceptible of being improved or prevented by inhibition of AChE may be under the scope of the invention.

FIG. 1 shows that constituents of Geranium oil (S)(~) citronellol and (R)(+)citronellol inhibit the peroxyl radical-induced oxidation of DCFH in primary microglial cells. Microglial cells were incubated for one h with (S)(−)citronellol (FIG. 1A) and (R)(+)citronellol (FIG. 1B). Primary cultures of microglial cells has been prepared according to Elmann et al., *Journal of Functional Foods* 2 (2010), pp. 18. As in Elmann et al. *BMC Complementary and Alternative Medicine* 2011, 11:98, the cultures of microglial cells were then preloaded with the non-fluorescent cell permeating compound, 27'-dichlorofluorescein diacetate (DCF-DA) for 30 min and washed with PBS, after which, 2,2'-Azobis (amidinopropane) (ABAP) (0.6 mM) was added and ROS levels were measured at the indicated time points. Each point on the graph represents mean±SEM of 2 experiments (n=8).

Figure 2:
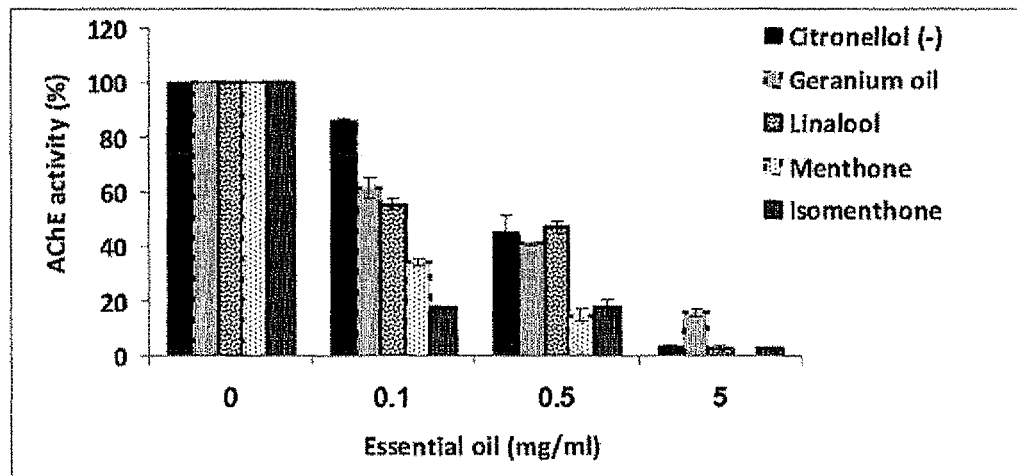
FIG. 2 shows the activity of acetyl cholinesterase after incubated with different constituents of geranium oil and with geranium oil itself.
Figure 3:
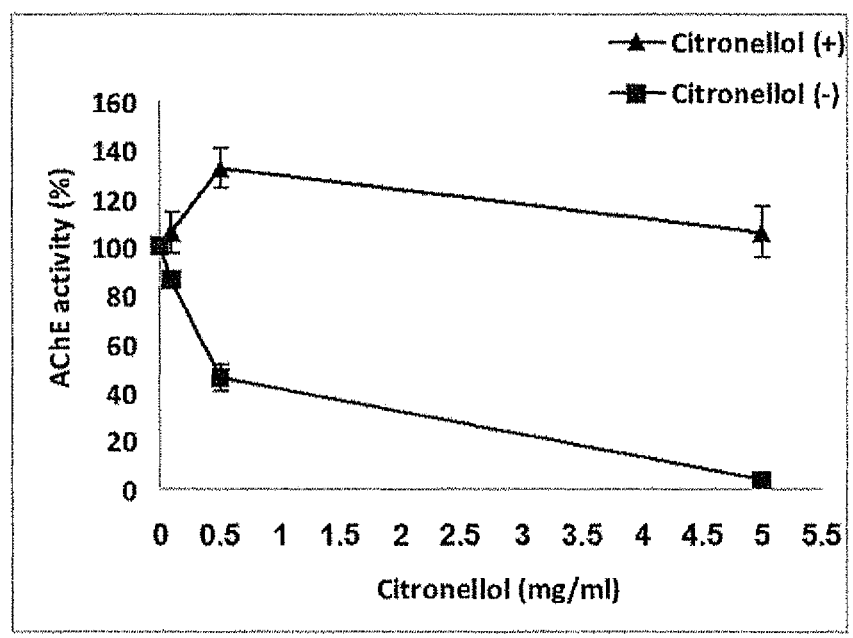
FIG. 3 shows the activity of acetyl cholinesterase after incubated with different enantiomers of citronellol.

As already mentioned, the inventors have unexpectedly found that only the enantiomer (S)(−)citronellol but not (R)(+)citronellol could inhibit the enzymatic activity of acetyl cholinesterase. The unexpectedness of these results is demonstrated for example, when comparing the effect of the same enantiomers on Reactive Oxygen Species (ROS) in microglial cells. While both enantiomers show significant reduction on ROS production (FIG. 1), only the enantiomer (S)(−)citronellol shows inhibition of enzymatic activity of acetyl cholinesterase (FIGS. 2 and 3).

The term "neurodegenerative condition or disease" is any condition or disease of, relating to, or being a progressive loss of neurologic functions.

The term "treating" as used herein in relation to neurodegenerative diseases in a subject is intended to mean that the compound, essential oil or extract or pharmaceutical composition of the invention reduces or abrogates the symptoms and/or cause of the neurodegenerative disease.

The term "prevention" as used herein in relation to neurodegenerative diseases in a subject is intended to mean that the compound, essential oil or extract or pharmaceutical composition of the invention substantially prevents and/or reduces the symptoms of the neurodegenerative diseases that would otherwise occur had the subject not been treated with the compound, essential oil or extract or pharmaceutical composition of the invention.

An "essential oil" is a product made by distillation with either water or steam or by mechanical processing of citrus rinds or by dry distillation of natural materials. Following the distillation, the essential oil is physically separated from the water phase.

In all therapeutic applications and unless otherwise noted, "*Pelargonium graveolens*" means *Pelargonium graveolens* essential oil or extract without separating plant's active constituents. "*Pelargonium graveolens* constituent" means a specific active constituent of *Pelargonium graveolens*.

Use of PET for Determining Whether Therapeutic Effects are Caused by Inhibition of AChE.

The positron emission tomographic (PET) technology to measure AChE functional activity offers the prospect of determining cholinergic innervation in vivo at the early stages of neurodegenerative disorders. For example acetyl cholinesterase (AChE) activity in the human AD-affected brain has been mapped using PET and 1-["C]methylpiperidin-4-yl propionate (["C]PMP) and N-["C]methylpiperidine-4-yl acetate radioligands (Bohnen et al., *Arch Neurol.* 2003; 60(12):1745-1748).

Therefore, for a neurodegenerative disease associated with decrease in levels of acetylcholine, the PET technique, combined with known tests unique for that neurodegenerative disease for assessing the condition of a subject may be used for determining whether improvement in a patient's condition is a result of AChE inhibition. Thus, this combined test (namely, (1) PET and (2) test for assessing the condition of a subject) may be made before and after administration of *P. graveolens* or constituents thereof. For example, for assessing the relationship between ratings of depressive symptoms and in vivo cortical acetylcholinesterase (AChE) activity in subjects with parkinson's disease (PD) and parkinsonian dementia (PDem), the PET may be combined with the Cornell Scale for Depression in Dementia (CSDD). For TBI, the Token Test and the Boston Naming Test may be administered during baseline testing together with PET. For dementia with Lewy Bodies and Parkinson's disease Dementia, the randomized controlled trials (RCTs) of DLB and PDD may be used together with PET. And, all of these combined tests may be made before and after administration of *P. graveolens* or constituents thereof.

The preparation of pharmaceutical compositions is known in the art, for example as described in Remington's Pharmaceutical Sciences (18th ed., Mack Publishing Co., Easton, Pa., 1990) and Pharmacopeia: National Formulary (Mack Publishing Company, Easton, Pa., 1984). For example, the compound may be prepared into a variety of pharmaceutical compositions in the form of, e.g., an aqueous solution, an oily preparation, a fatty emulsion, an emulsion, a gel, etc., and these preparations may be administered as intramuscular or subcutaneous injection or as injection to an organ, or as an embedded preparation or as a transmucosal preparation through nasal cavity, rectum, uterus, vagina, lung, etc. The composition may be administered in the form of oral preparations (for example solid preparations such as tablets, capsules, granules or powders; liquid preparations such as syrup, emulsions or suspensions). Compositions containing the compound may also contain a preservative, stabiliser, dispersing agent, pH controller or isotonic agent. Examples of suitable preservatives are glycerin, propylene glycol, phenol or benzyl alcohol. Examples of suitable stabilisers are dextran, gelatin, a-tocopherol acetate or alpha-thioglycerin. Examples of suitable dispersing agents include polyoxyethylene (20), sorbitan mono-oleate (Tween 80), sorbitan sesquioleate (Span 30), polyoxyethylene (160) polyoxypropylene (30) glycol (Pluronic F68) or polyoxyethylene hydrogenated castor oil 60. Examples of suitable pH controllers include hydrochloric acid, sodium hydroxide and the like. Examples of suitable isotonic agents are glucose, D-sorbitol or D-mannitol. The composition may also contain other constituents or additives such as a pharmaceutically acceptable carrier, diluent, excipient, suspending agent, lubricating agent, adjuvant, vehicle, delivery system, emulsifier, disintegrant, absorbent, preservative, surfactant, colorant, flavorant or sweetener, taking into account the physical and chemical properties of the compound being administered.

In another embodiment, *P. graveolens* essential oil is the sole active ingredient in a composition for treating neurodegenerative disease such as Parkinson's disease.

In a yet another embodiment, any one of the *Pelargonium graveolens* constituents selected from a group consisting of: (S)(−)citronellol, linalool, menthone and isomenthone or any combination thereof is/are the sole active ingredient in a composition for treating neurodegenerative disease.

In another embodiment, the present invention provides pharmaceutical compositions for use in the treatment of Parkinson's disease. In another embodiment, the present invention provides pharmaceutical compositions for use in preventing deterioration of Parkinson's disease. This prevention is reflected by cessation of neuronal cells death in a patient showing Parkinson's disease symptoms. Results disclosed herewith for prevention of neuronal cells death (see Example 7) is surprising. The direct and significant effect on the prevention of dopaminergic nerve cells was not expected by the inventors.

The MPTP Model

In order to demonstrate the therapeutic effect of *P. graveolens* in treating Parkinson's disease, the inventors have used the MPTP model. Among the various toxic models of PD, the MPTP (1-methyl-4-phenyl-1,2,3,6-tetrahydropyridine) model has become the most commonly used. MPTP is the only known dopaminergic neurotoxin capable of causing a clinical picture in both humans and monkeys indistinguishable from PD. Second, although handling MPTP requires a series of precautions, its use is not otherwise technically challenging: it does not require any particular equipment such as a stereotaxic frame, nor does it require surgery on live animals as for 6-hydroxydopamine or rotenone. And third, MPTP produces a reliable and reproducible lesion of the nigrostriatal dopaminergic pathway after its systemic administration, which is often not the case for other documented poisons. MPTP causes parkinsonian features in humans and primates as a result of dopaminergic degenerations in the nigrostriatal pathway. Its neurotoxic effects also appear to involve energy depletion and free radical generation. MPTP is converted to its metabolite MPP+ by monoamine oxidase B (MAO-B). MPP+ is selectively accumulated by high affinity dopamine transporters and taken up into the mitochondria of dopaminergic neurons, where it disrupts oxidative phosphorylation by inhibiting complex I of the mitochondrial electron transport chain. This leads to impairment of ATP production, elevated intracellular calcium levels, and free radical generation. Thereby exhibiting dopaminergic neurotoxicity. Therefore, MPTP is widely used as a tool to study the molecular events that lead to degeneration of dopaminergic neurons in animal model of Parkinson's disease and to test potential neuroprotective agents.

Preclinical Evaluation of Geranium (*P. graveolens*) Oil in the MPTP Induced Model of Parkinson's Disease in Mice. In a demonstration of the present invention as applied to mice, the preclinical efficacy of geranium (*P. graveolens*) oil was evaluated in the 1-methyl-4-phenyl-1,2,3,6-tetrahydropyridine (MPTP) induced model of Parkinson's disease in C57BL/6 mice (The Parkinson's disease afflicted mice will be called from now on "MPTP PD mice"). MPTP was injected to C57BL/6 (11-13 mice/group) intraperitoneally (i.p.) daily during the initial 5 days (day 1-5). Geranium oil was administered to MPTP PD mice on days 1-11 by oral gavage or by subcutaneous injection. At the first 5 days, the oil was administered 30 min before MPTP administration. The effect of geranium oil on motor coordination and cognitive function in experimentally PD-induced mice was evaluated using the Rota Rod and the social recognition tests, respectively. At the end of the study, the subjects' brains were removed and analyzed for neuronal cell loss in the substantia nigra.

As outlined, an accelerating rotarod is used to measure motor coordination in mice. Mice have to keep their balance on a horizontal rotating rod, and rotation speed is accelerated from 4 to 20 rpm over 5 min. A trial starts when the mouse is placed on rotating rod, and it stops when the mouse falls down or when 5 min are completed. Each mouse is experiencing 3 trials per day with an intertrial interval of 10 min.

EXAMPLES

All results disclosed in the Examples herewith referring to geranium oil, have been obtained with the essential oil of the plant *Pelargonium graveolens* (*P. graveolens*).

Example 1—*P. Graveolens* Constituents that Inhibit Acetyl Cholinesterase Activity In this Example, Human erythrocytes acetyl cholinesterase (AChE) was incubated with different concentrations of geranium oil or each of its constituents.

Preparation of Essential Oils and GC-MS Analyses.

*P. graveolens* was grown at the Newe Ya'ar Agricultural Experimental Station, under cultivated conditions. Seeds were taken from cooled seed storage and were sown at Newe Ya'ar. The plant was cultivated in local clayey soil under drip irrigation, as described in Dudai et al, (2003), *Flavour and Fragrance Journal*, 18, 334-337. Plant samples of at least 5 kg were steam-distilled in a 130 L direct steam pilot plant apparatus for 1 h. The essential oils were diluted with petroleum ether and were injected to the a GC-MS, MSD (Agilent Technologies, Palo Alto, Calif., USA) with an autosampler Combi Pal (CTC Analytics, Zwingen, Switzerland) equipped with a Rtx-5SIL MS (30 m×0.25 mm i.d.× 0.25 lm) fused-silica capillary column (Restek, Bellefonte, Pa., USA). Helium, at a constant pressure of 14.14 psi and a linear velocity of 47 $cm^4$, was used as carrier gas. The injector was kept at 250° C. and set for the 1:50 split mode. The transfer line was kept at 280° C. The column was maintained at 50° C. for 1 min, then programmed to 190° C. at 5° $C.min^{-1}$, then to 260° C. at 10° C. $min^{-1}$. The MSD was operated in the electron ionization mode at 70 eV, in the m/z range of 42-350. Identification of compounds was performed by comparing their relative retention indices and mass spectra with those of authentic samples, supplemented with the NIST 98 and HPCH 2205 GC-MS libraries.

Enzymatic Activity.

In the results shown in FIG. 2, the different constituents were incubated with human erythrocytes' acetyl cholinesterase (25 mU/mL). The activity of acetyl cholinesterase was determined using a commercially available kit (acetyl cholinesterase fluorescent activity assay kit, Arbor assays). FIG. 2 demonstrates that geranium oil, (S)(−)-citronellol, linalool, menthone and isomenthone inhibited the enzymatic activity.

Example 2—Difference Between Enantiomers of Citronellol on AChE Activity

Geranium oil contains the two enantiomers of citronellol [(R)(+):(S)(−)] in a ratio of ~80:20. Thus, inventors have tested the effect of both enantiomers on the enzymatic activity. As noted, only the enantiomer (S)(−)citronellol but not (R)(+)citronellol could inhibit the enzymatic activity. FIG. 3 shows that the difference between enantiomers of citronellol on AChE activity is significant. The different enantiomers of citronellol were incubated with human erythrocytes' acetyl cholinesterase (25 mU/raL). The enzymatic activity was determined using a commercially available kit (acetyl cholinesterase fluorescent activity assay kit. Arbor assays).

Figure 4:
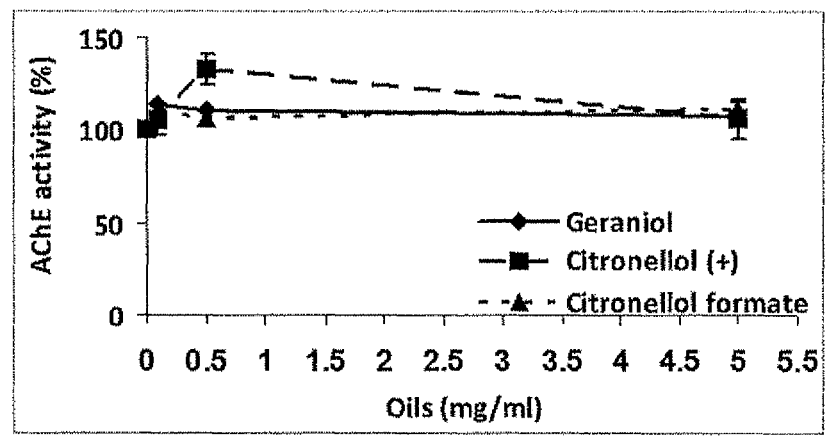
FIG. 4 shows the effect of Gercniol, Citronellol(+) and Citronellol formate on the activity of the human erythrocytes' acetyl cholinesterase.

Example 3—*P. Graveolens* Constituents that does not Inhibit Acetyl Cholinesterase Activity In FIG. 4, different constituents of geranium oil (Geraniol, Citronellol (+) and Citronellol formate) were incubated with human erythrocytes' acetyl cholinesterase (25 mU/mL). The activity of acetyl cholinesterase was determined using a commercially available kit (acetyl cholinesterase fluorescent activity assay kit, Arbor assays). According to FIG. 4, none of the constituents geraniol, Citronellol (+) and citronellol formate could inhibit AChE activity.

Example 4—Effect of Geranium Oil on Body Weights of MPTP-PD Mice

Figure 5:
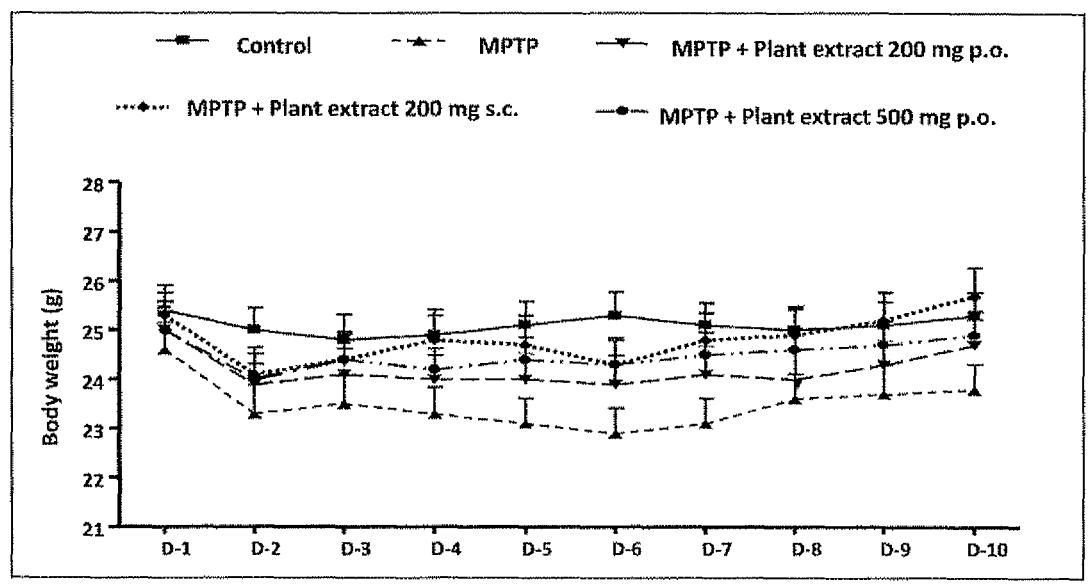
FIG. 5 shows the effect of geranium oil on body weights of MPTP-PD mice.

Body weight of MPTP-PD mice was statistically significant lower than that of control healthy mice. Treatment with geranium oil blocked the reduction in body weight observed in MPTP-PD mice. FIG. 5 illustrates effect of geranium oil on the body weights of MPTP PD mice. Body weights were recorded prior to dosing and every day during dosing, throughout the entire study.

MPTP formulation: Dissolve 100 mg MPTP in 5 ml of water for injection and use this stoke solution for MPTP (20 mg/ml) dose level preparation; Dose volume: 10 ml/kg and Dose level: 30 mg/kg; Dilute stock MPTP solution (20 mg/ml) to 4 mg/ml solution with water; Prepare sufficient volume for each group; Prepare sufficient volume for each group.

Test Items and Vehicle formulation: Stock solution of the test item 1000 mg/ml; Dilute the test item stock solution as follows: Prepare 4 ml of 20 mg/ml by adding 80 μl stock solution into 3.92 ml MCT and mix well and prepare 2 ml of 50 mg/ml adding 0.1 ml stock solution into 1.9 ml MCT and mix well.

Example 5—Effect of Geranium Oil on Rota Rod (RR) Performance of MPTP PD Mice

The Rota Rod (RR) performance used, reflects motor coordination of mice. All animals started at 3 rpm at 0 min and accelerated from 4 to 20 rpm over 5 min with each mouse experiencing three trials per day with an intertrial interval of 10 min. The average latency of each mouse was calculated. All advancements were according to the set time lines and were approximated. The latency time to fall was measured.

A statistically significant reduction in the time spent on the RR on day 11 of the study, was observed in the MPTP PD mice that were treated with vehicle, compared to control healthy mice (FIG. 6A). This observation was also supported by a similar statistically significant reduction in the distance traveled on the RR (FIG. 6B). Treatment with geranium oil significantly increased RR latency and distance of MPTP PD mice, compared to vehicle treated MPTP PD mice (FIGS. 6A and B).

Figure 6:
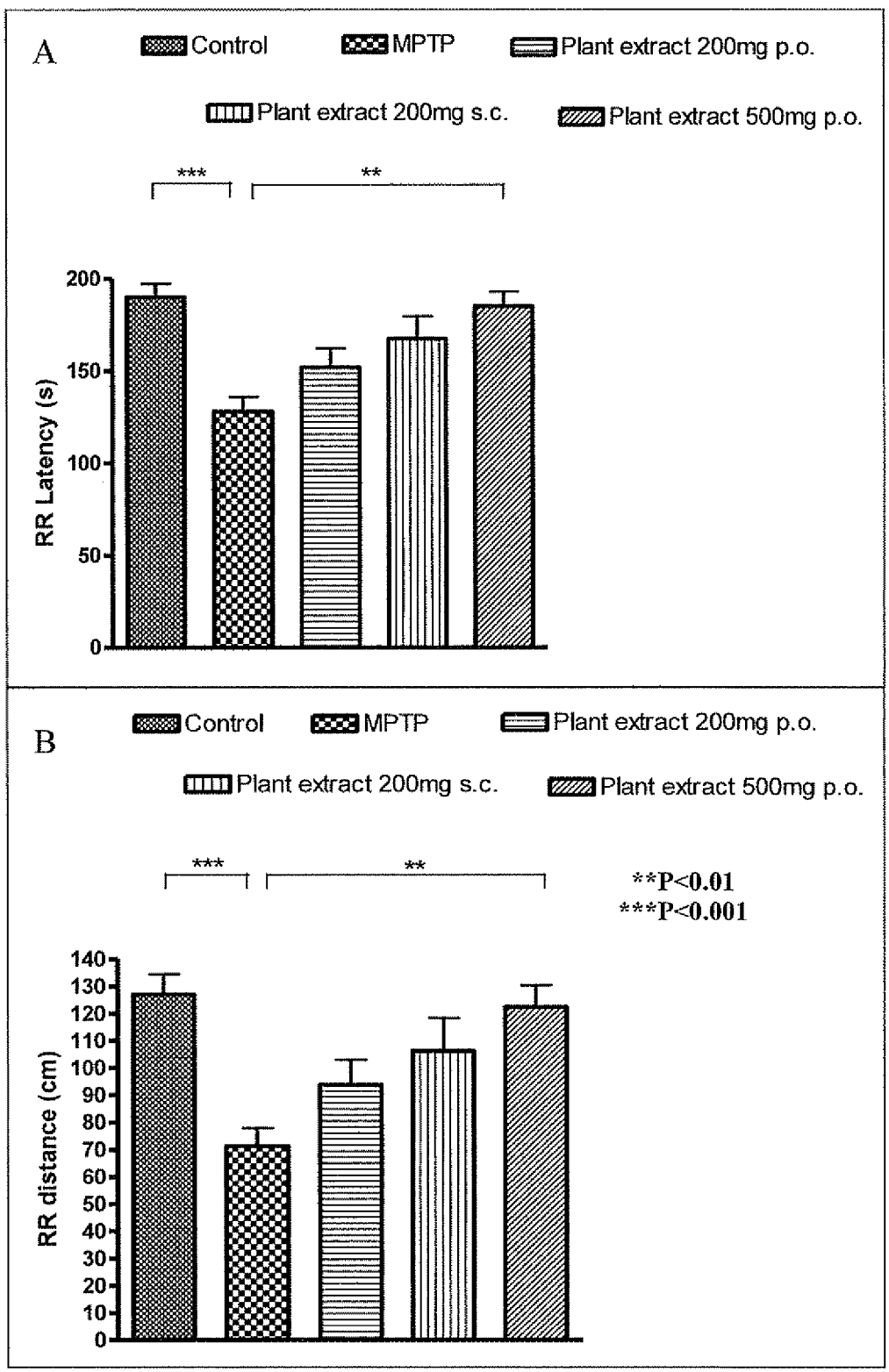
FIG. 6 shows the effect of geranium oil on Rota-Rod latency (FIG. 6A) and distance (FIG. 6B) of MPTP PD mice.

FIG. 6 demonstrates the effect of geranium oil on Rota-Rod latency and distance of MPTP PD mice. Mice were trained on Rota-Rod, 3 trials/day, at days (−7), (−5) and (−3), and were tested at day 11 for their RR performance. Results were analyzed using two-way ANOVA repeated measurements, post hoc Bonferroni post tests. *($p<0.001$), ($p<0.01$).

Example 6—Effect of Geranium Oil on Social Recognition Test in MPTP PD Mice

Figure 7:
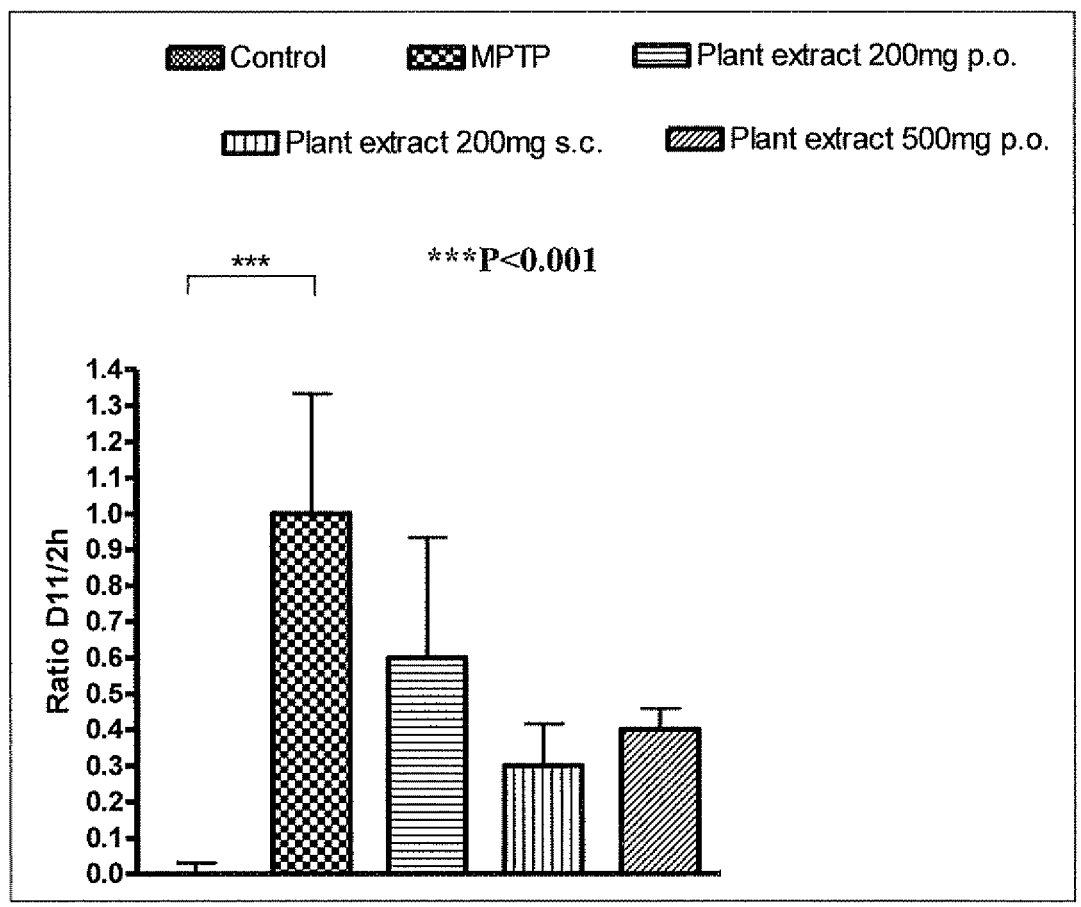
FIG. 7 shows the effect of geranium oil on social recognition of MPTP-induced Parkinson's mice.

Both MPTiMnduced PD mice that were treated with geranium oil and control healthy mice showed a social memory effect by spending less time investigating the same juvenile animal following subsequent exposure. In contrast, the investigative duration of the vehicle-treated MPTP PD mice was significantly higher following the subsequent juvenile exposure, compared to the control healthy mice and to geranium oil treated MPTP PD mice. Interaction ratio, reflecting social recognition memory improvement, of vehicle-treated MPTP PD animals was significantly higher, compared to healthy control mice and to MPTP PD mice that were treated with geranium oil (FIG. 7).

The social recognition test measures memory on the basis of olfactory cues. FIG. 7 illustrates the effect of geranium oil on social recognition of MPTP-induced Parkinson's mice. The mouse was individually housed 1 h before starting the test to isolate their odors. An adult mouse and a single juvenile mouse were placed in an arena for a period of 5 min. During the first (T-1) interactive trial, the adult exhibits investigative behavior that includes close following, sniffing or grooming the younger mouse. The amount of time that the adult spent investigating the younger mouse was scored by investigator with stop clocks in seconds. The juvenile and the adult mice were then removed and returned to their cages. Second (T-2) interactive trial was conducted 120 min later in the same arena, and investigative behavior of the adult mouse was again monitored and recorded. A single memory test trial was performed on day 10. Recognition ratios of time spent investigating the familiar juvenile in T-2 divided by the time spent investigating the juvenile in T-1 was calculated (ratio D11/2 h). Results were analyzed by two-way ANOVA repeated measurements, post hoc Bonferroni post tests. ***($p<0.001$).

Figure 8:
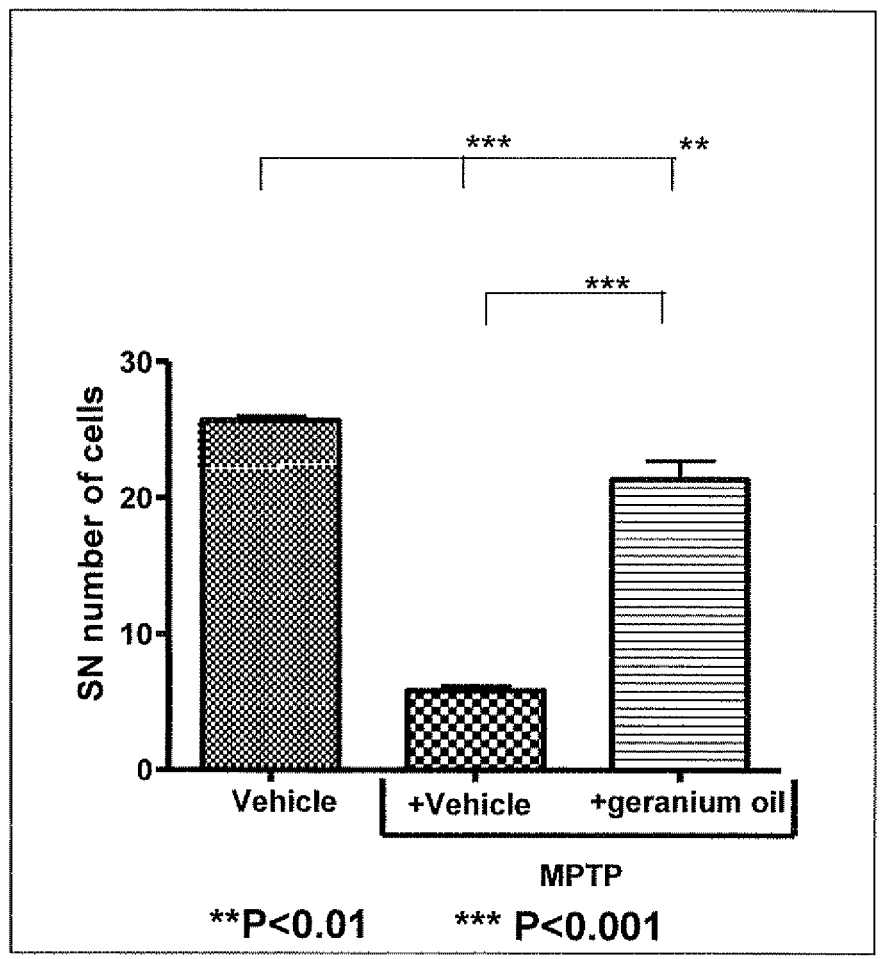
FIG. 8 shows the effect of geranium oil on the number of dopaminergic neurons in the substantia nigra.

Example 7—Effect of Treatment with Geranium Oil on the Number of Dopaminergic Neurons in the Substantia Nigra FIG. 8 shows the effect of geranium oil on the number of dopaminergic neurons in the substantia nigra. Brains of all mice from (i) control healthy mice (ii) MPTP PD mice and (iii) MPTP PD mice that were treated orally with 500 mg/kg geranium oil, were fixed, sectioned, immunostained and the number of dopaminergic neurons in the substantia nigra was counted. As can be seen in FIG. 8, the number of dopaminergic neurons in the substantia nigra was markedly reduced in brains of the MPTP PD mice in comparison to control healthy mice. However, treatment of MPTP PD mice with geranium oil prevented the observed neuronal cell death. Upon study termination on day 12, mice were euthanatized with $CO_2$ asphyxiation. All brains were rapidly removed and stored in 10% buffered formalin solution. Three fields were sampled from each mouse. One way analysis of variance was employed to compare between the different groups. Vehicle means the solvent with which the geranium oil was diluted; in this case—MCT.

All patents, patent publications, and non-patent publications cited are incorporated by reference herein.

What is claimed is:

1. A method for treating a neurodegenerative condition, comprising administering to a subject in need thereof a composition comprising, as the sole active ingredient, geranium oil extracted from *Pelargonium graveolens* in an amount effective for the treatment of the neurodegenerative condition, wherein said neurodegenerative condition is selected from the group consisting of Alzheimer's disease, Parkinson's disease, Parkinsonian dementia (PDem), Parkinson's disease dementia (PDD), dementia with Lewy bodies (DLB), anorexia nervosa, traumatic brain injury (TBI), and Parkinson's disease falling short of dementia (CIND-PD).

2. The method of claim 1, wherein said neurodegenerative condition is characterized by death of dopaminergic neurons.

3. The method of claim 1, wherein said treating a neurodegenerative condition is by affecting the levels of acetylcholine.

4. The method of claim 3, wherein said composition affects the levels of acetylcholine by inhibiting the enzymatic activity of acetylcholinesterase (AchE).

5. The method of claim 1, wherein said composition is prepared from a stock solution having a concentration of 1000 mg geranium oil per ml.

* * * * *